United States Patent [19]
Feldman

[11] Patent Number: 5,578,019
[45] Date of Patent: Nov. 26, 1996

[54] EYE DROP APPLICATOR

[76] Inventor: Edward L. Feldman, 232 Cedar Park Cir., Sarasota, Fla. 34242

[21] Appl. No.: 478,724

[22] Filed: Jun. 7, 1995

[51] Int. Cl.⁶ .............. A61M 35/00; B65D 47/18
[52] U.S. Cl. .............. 604/295; 604/300; 222/420
[58] Field of Search ................. 604/295, 298, 604/300, 301, 302; 220/254, 252, 253, 715; 222/420, 421; 215/228, 237, 238, 311

[56] References Cited

U.S. PATENT DOCUMENTS

| | | | |
|---|---|---|---|
| 3,058,466 | 10/1962 | Routsong | 128/233 |
| 3,279,466 | 10/1966 | Mings | 128/233 |
| 3,598,121 | 8/1971 | Lelicoff | 128/233 |
| 3,872,866 | 3/1975 | Lelicoff | 128/233 |
| 4,002,168 | 1/1977 | Petterson | 128/233 |
| 4,085,750 | 4/1978 | Bosshold | 128/233 |
| 4,543,096 | 9/1985 | Keene | 604/300 |
| 4,605,398 | 8/1986 | Herrick | 604/300 |
| 4,834,727 | 5/1989 | Cope | 604/300 |
| 4,973,322 | 11/1990 | Jewart | 604/300 |
| 5,064,420 | 11/1991 | Clarke et al. | 604/295 |
| 5,154,710 | 10/1992 | Williams | 604/301 |
| 5,207,657 | 5/1993 | Gibilisco | 604/295 |
| 5,295,981 | 3/1994 | Smith et al. | 604/301 |

Primary Examiner—John G. Weiss
Assistant Examiner—David J. Cho
Attorney, Agent, or Firm—Oppedahl & Larson

[57] ABSTRACT

A bottle for administering liquid eye drops, comprising:

(a) a container for holding the liquid eye drops;

(b) a dispensing assembly, and (c) a closure assembly. The dispensing assembly is coupled to the container and has a passage therethrough for dispensing of the liquid eye drops from the container. The closure assembly is pivotally mounted on the dispensing assembly and moves between a closed or storage position in which the passage in the dispensing assembly is sealed by a closure seat disposed on the interior surface of the closure assembly, and an open position in which the passage is open for dispensing eye drops. An eye lid retractor is attached to the exterior surface of the closure assembly for retracting the lower eye lid of an individual to whom the eye drops are being administered. The dispensing assembly and the closure assembly may also be provided as a separate cap unit for attachment to a conventional eye drop bottle, and such a cap is a further aspect of the present invention.

18 Claims, 3 Drawing Sheets

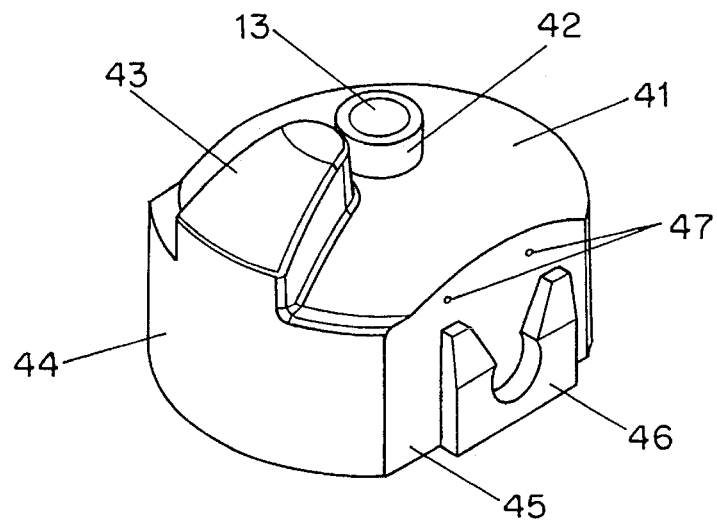
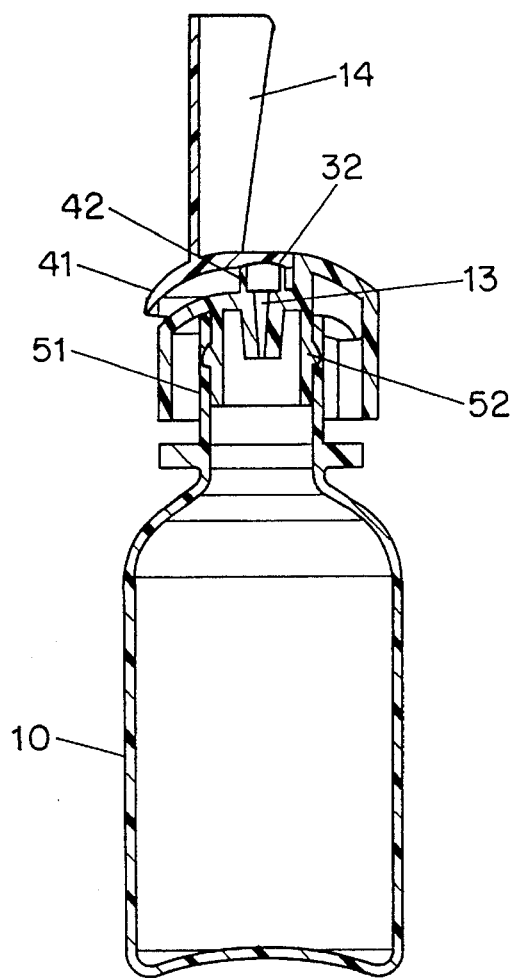
FIG. 5

EYE DROP APPLICATOR

BACKGROUND OF THE INVENTION

This application relates to an improved bottle for dispensing liquid eye drops.

Liquid eye drops are commonly used to introduce over-the-counter and prescription medications into the eyes of human patients. The most common container in which these eye drops are supplied is simply a bottle with a tapered dropper. Notwithstanding the ubiquitous nature of such containers, it has been recognized that a container with a tapered nozzle does not provide for optimum means for administering drops into the eye. In fact, people using such bottles frequently bring their fingers into contact with their eye and eye lids to hold the eye open for administration of the eye drops which increases the risk of eye infection. In addition, traditional elongated eye dropper bottle tips may come in contact with eye secretions increasing the risk of contamination. Furthermore, the tendency of many persons to blink or flinch away during the application of the eye drops makes the administration of a consistent dosage of eye drops difficult for many.

Many different styles of eye drop bottles have been proposed to overcome the difficulties of the standard eye drop bottle. For example, U.S. Pat. Nos. 3,058,466; 3,279,466; 3,598;121; 3,872,866; 4,085,750; 4,543,096; 4,605,398; 4,834,727; 4,973,322; 5,064,420; 5,154,710 and 5,295,981, which are incorporated herein by reference, each disclose removable attachments which are affixed to a conventional dropper bottle. None of these devices have found commercial acceptance, however, perhaps because they all are complicated designs involving several separable parts and removable lids. U.S. Pat. No. 4,002,168, which is incorporated herein by reference, discloses a variety of different designs for an eye drop applicator which incorporate eye lid retractors of various types. In one embodiment, the eye lid retractor is pivotally moveable with respect to the dispensing orifice, and is said to achieve sealing of the orifice when pivoted into a closed position. No structure for accomplishing this sealing is disclosed, however.

It is an object of the present invention to provide an improved design for an eye drop applicator with an eye lid retractor, and in particular to provide a design for an eye drop applicator in which no separation or assembly of pieces is necessary to use or store the applicator.

SUMMARY OF THE INVENTION

In accordance with the present invention, there is provided a bottle for administering liquid eye drops, comprising:

(a) a container for holding the liquid eye drops;

(b) a dispensing assembly, said dispensing assembly being coupled to the container and having a passage therethrough for dispensing of the liquid eye drops from the container; and (c) a closure assembly comprising a base portion having means for sealing the passage in the dispensing assembly disposed on an interior surface thereof and means for retracting the lower eye lid of an individual to whom the eye drops are being administered disposed on the exterior surface thereof, wherein said closure assembly is pivotally mounted on the dispensing assembly to permit movement of the closure assembly between a first position in which the passage in the dispensing assembly is sealed by the means for sealing the passage in the dispensing assembly and a second position in which the passage in the dispensing assembly is open to permit dispensing of the liquid eye drops. The dispensing assembly and the closure assembly may also be provided as a separate unit for attachment to a conventional eye drop bottle, and such a cap is a further aspect of the present invention.

BRIEF DESCRIPTION OF THE DRAWINGS

FIG. 4 shows an exterior view of a dispensing assembly in accordance with the invention; and FIG. 5 shows a cross section of an applicator bottle in accordance with the invention.

DETAILED DESCRIPTION OF THE INVENTION

Figure 1A:
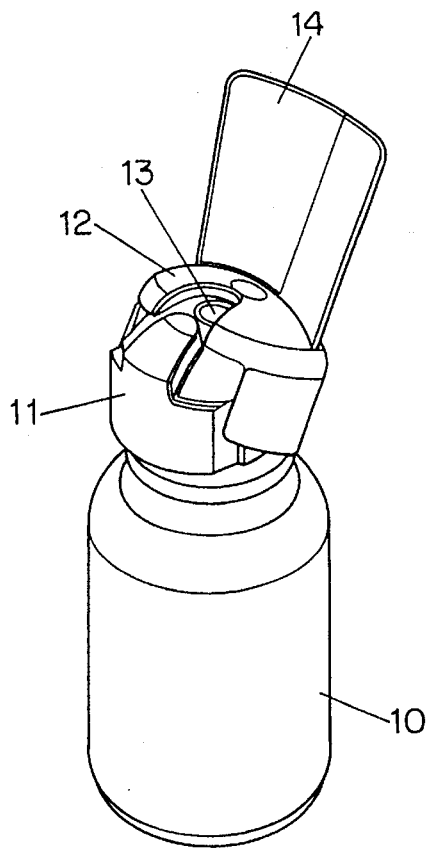
FIGS. 1A and 1B show an eye drop bottle in accordance with the invention with the closure assembly in the open and closed positions, respectively.
Figure 1B:
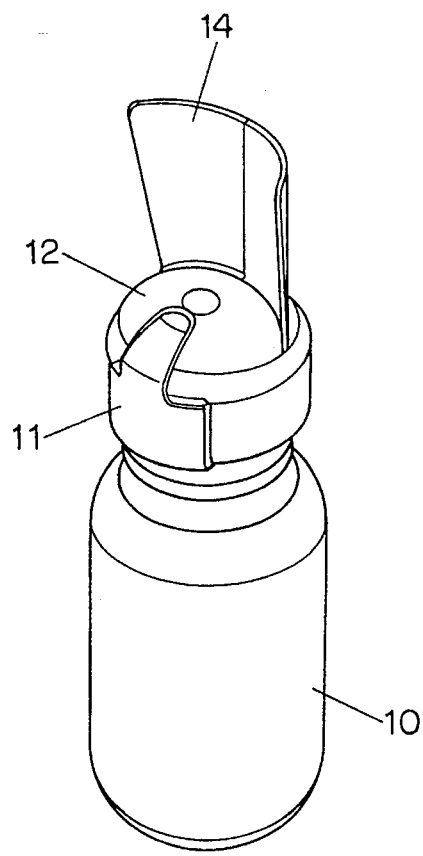

The present invention provides an eye drop applicator with an easy to use eye lid retractor. As shown in FIGS. 1A and 1B, the eye drop bottle of the invention comprises a container 10, a dispensing assembly 11 and a closure assembly 12. The dispensing assembly 11 is coupled to the container 10 and has a passage 13 extending therethrough for dispensing liquid eye drops from the container. The closure assembly 12 is pivotally mounted on the dispensing assembly 11 and is moveable between an open position, shown in FIG. 1A and a closed position shown in FIG. 1B.

In the open position, the closure assembly 12 is pivoted away from the axis of the container as a whole, exposing the end of passage 13 and permitting the dispensing of eye drops. In addition, the eye lid retractor 14 is disposed in a position for effective application of eye drops when the eye lid retractor 14 is placed against the lower lid area of a user, i.e., the lid retractor is angled for correct drop placement. The exact angle necessary to achieve this result will depend on the length of the retractor and the lateral separation between the passage 13 and the retractor 14. In the closed position (FIG. 1B), the closure assembly 12 covers the open end of the passage 13 and seals the applicator for storage.

Figure 2A:
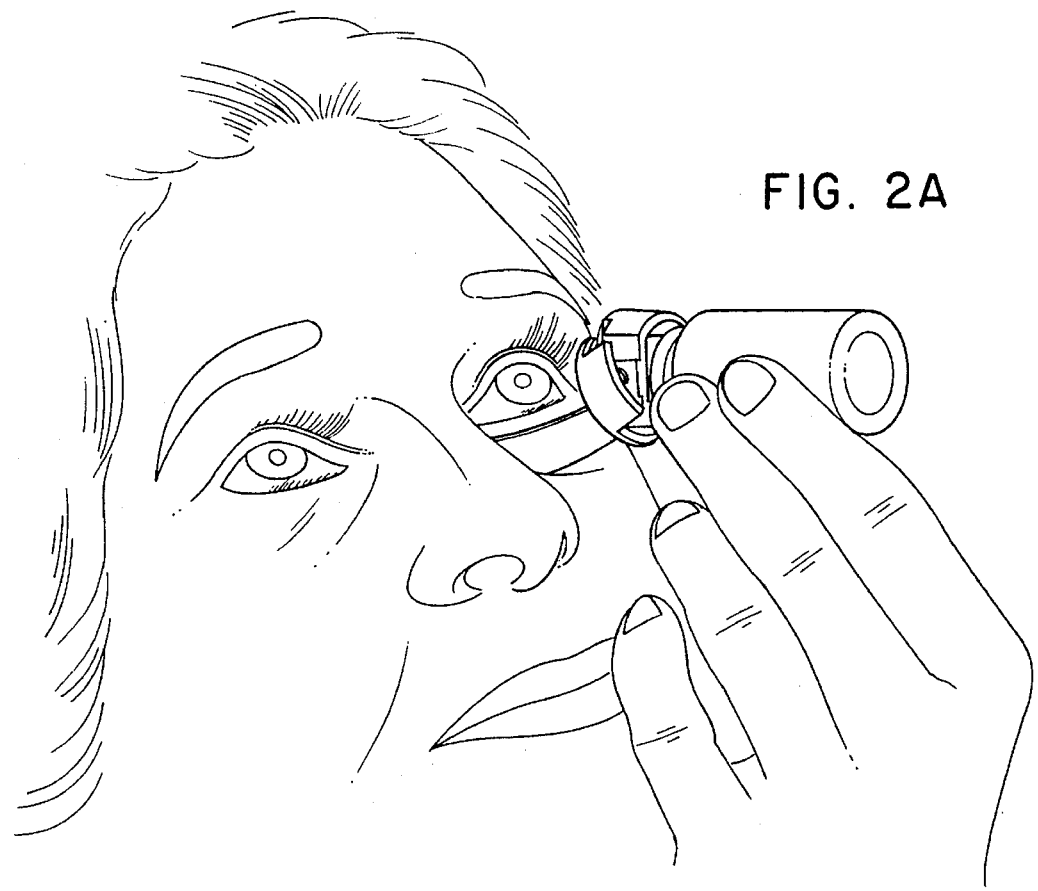
FIG. 2A and 2B shows an individual using an eye drop applicator in accordance with the invention.
Figure 2B:
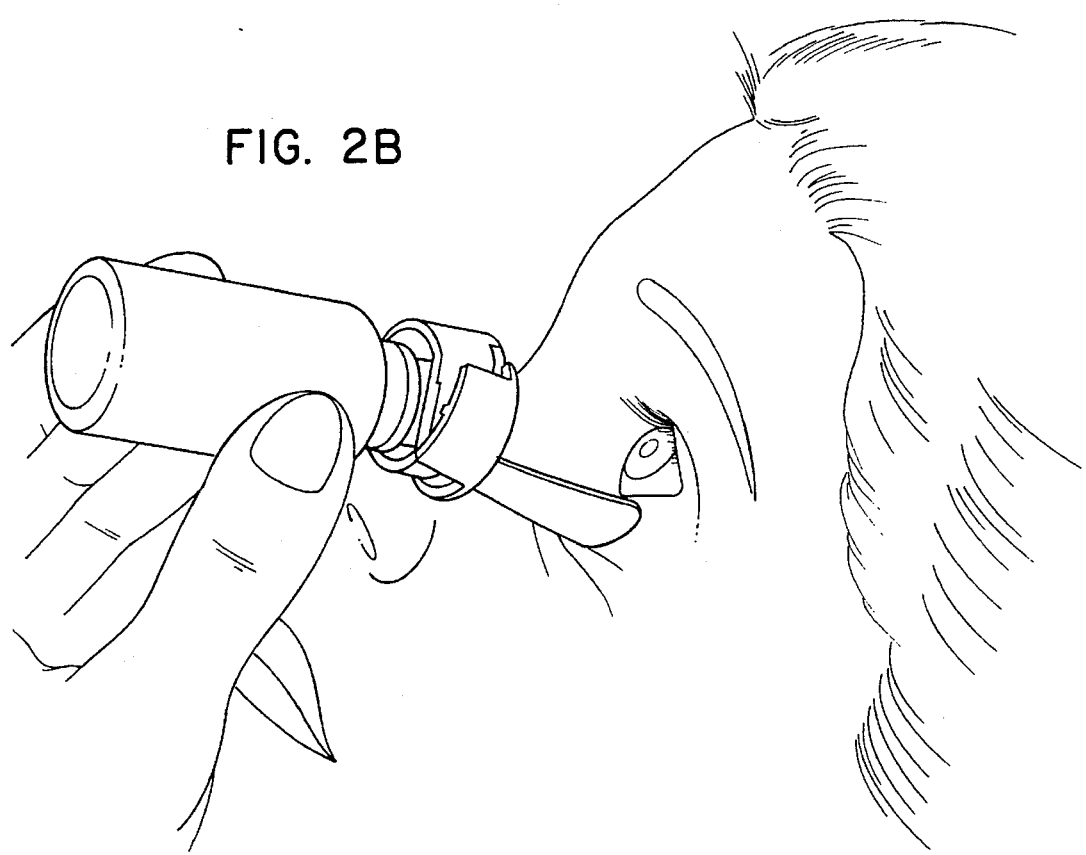

FIG. 2A and 2B shows the manner in which an applicator in accordance with the invention is used. As shown, the user tips his or her head slightly backwards, and places the eye lid retractor 14 against the lower lid 21 with the closure assembly in the open position. This everts the lower eye lid away from the eye, opening the cul-de-sac between the lower lid ands the globe of the eye, and brings the opening of the passage 13 into a proper position relative to the eye so that when drops are dispensed from the applicator they will enter the eye. Dispensing of drops can then be accomplished by squeezing the container 10. The retractor can also be used to apply pressure to the lower lid after drop application to limit the entry of eye drops into the tear drainage system.

Figure 3A:
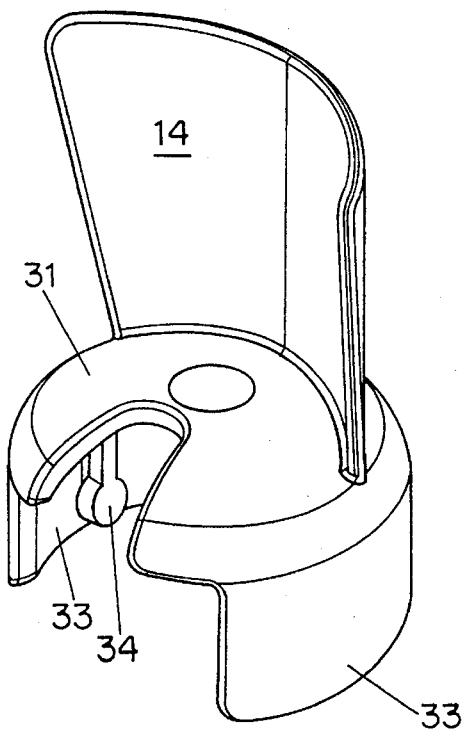
FIGS. 3A and 3B shows a closure assembly in accordance with the invention.
Figure 3B:
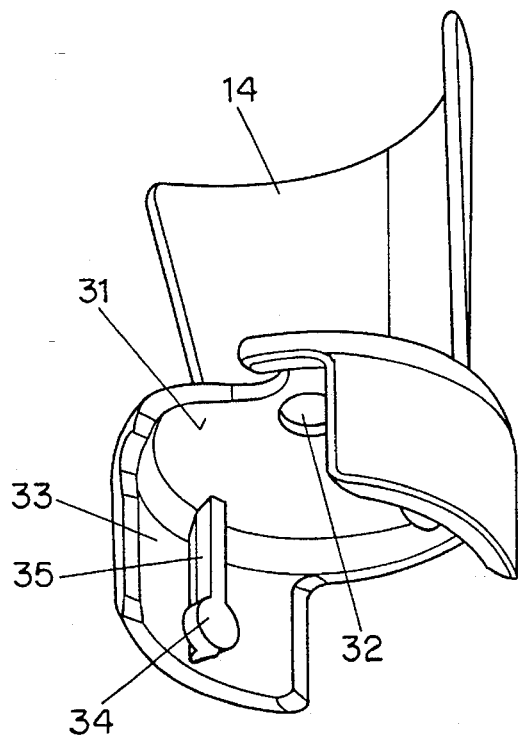

FIGS. 3A and 3B are top and bottom perspective views showing the closure assembly of the invention in greater detail. As shown, the closure assembly has a base portion formed from a substantially circular and domed top portion and two skirts 33. An eye lid retractor 14 is attached to the exterior surface of the top portion 31. A notch is taken out of the top portion 31 extending from the edge of the top portion to a point just short of the center. In the center of the underside of the top portion is a closure seat 32 which acts to engage and seal the opening of the passage 13 through the dispensing assembly 11 when the closure assembly is in the closed or storage position.

The closure seat 32 may be a flexible and compressible material which is affixed to interior surface of the top portion. Preferred materials for this purpose are synthetic rubbers, elastomers, and photopolymerizable resins useful in implementing computer-assisted-designs. Alternatively, the closure seat may be a defined region on the interior surface of top portion which interacts with a flexible and compressible material on the dispensing assembly to seal the passage through the dispensing assembly.

The two opposed skirts 33 extend downward from the edges of the top portion 31 and are symmetrically disposed on either side of the base portion with respect to the eye lid retractor, leaving the edges of the top portion along the front and the back of the base portion free. Bearing members 34 are disposed on the interior surface of each skirt for pivoting articulation with a bearing seat 46 on the dispensing assembly (See FIG. 4). The bearing member 34 may also include a detent 35 for fixing the closure assembly in either the open or closed position.

The eye lid retractor 14 is shown as a spatulate member which is curved to conform to the average curvature of the human lower lid area. It will be understood, however, that other designs for the eye lid retractor, including open loop designs, could be employed.

FIG. 4 shows an top perspective view of a dispensing assembly in accordance with the invention. The dispensing assembly has a substantially circular top 41 on which is disposed a dispensing nozzle 42 surrounding the end of passage 13 which extends through the dispensing assembly, and a dirt seal 43.

The dispensing nozzle 42 engages with the closure seat 32 of the closure assembly to seal the passage 13 when the closure assembly is in the closed or storage position. Advantageously, the dispensing nozzle 42 will have a soft compressible sealing ring affixed to the end thereof for this purpose.

The dirt seal 43 extends upwards from the top portion 41 of the dispensing assembly and is sized to fit within the notch in the top 31 of the closure assembly. The purpose of the dirt seal 43 is to prevent contamination of the dispensing nozzle 42 when the applicator is not in use. The dirt seal 43 and the top portion 12 may snap together using a detent to fix the applicator in a closed position for storage.

Extending downward from the top 41 of the dispensing assembly is a skirt 44. The skirt 44 has two opposed surfaces 45 which are flattened and on which the bearing seats 46 and optional detents 47 are disposed. Bearing members 34 snap into bearing seats 46 which permit pivoting movement of the closure assembly between two defined positions, while holding the closure assembly to the dispensing assembly. Male and female detents 35 and 47 interact to fix the closure assembly into one of the two positions. Of course, it will be understood that the term "fix" in this case does not imply any degree of permanence, but only indicates the fact that the closure assembly is held in one of the two defined positions until some force is applied to move the closure assembly.

FIG. 5 shows a cross-section of an applicator bottle in accordance with the invention in a plane which bisects the eye lid retractor 14 when the closure assembly is in the closed position. In this embodiment of the invention, the dispensing assembly is coupled to the neck 51 of the container 10 by a tightly fitting stopper portion 52. Alternative means for coupling the dispenser assembly to the container include threaded couplings and glued joints. In addition, the dispensing assembly may be formed as an integral part of the container.

FIG. 5 also shows the sealing interaction of the closure seat 32 and the dispensing nozzle 42 when the dispensing assembly is in the closed or storage position. As shown in FIG. 5, a flexible closure seat 42 is disposed on the interior surface of the top 41 of the closure assembly.

While the foregoing discussion has been directed to a complete applicator bottle, it will be apparent to those skilled in the art that novel features of the present invention reside in the combination of the dispensing assembly and the closure assembly, and that such a cap combining these two assemblies could be advantageously placed on a conventional eye drop bottle provided that a compatible coupling means were included. Thus, a further aspect of the invention is a cap for an eye drop bottle. The cap comprises a dispensing assembly which includes means for coupling the dispensing assembly to a container for holding eye drops and having a passage therethrough for dispensing of the liquid eye drops from the container. Suitable means for coupling the dispensing assembly to the bottle will depend on the nature of the bottle but will generally be a threaded channel compatible with the threads Of the bottle or a stopper. The cap of the invention further comprises a closure assembly. As in the case of the complete bottle of the invention, the closure assembly has means for sealing the passage in the dispensing assembly and means for retracting the lower eye lid of an individual to whom the eye drops are being administered, wherein said closure assembly is pivotally mounted on the dispensing assembly to permit movement of the closure assembly between a first position in which the passage in the dispensing assembly is sealed by the means for sealing the passage in the dispensing assembly and a second position in which the passage in the dispensing assembly is open to permit dispensing of the liquid eye drops.

The applicator bottle and the cap of the invention are advantageously made from plastics such as polyethylene, polypropylene, polyester or photopolymerizable resins suitable for implementing and constructing computer-assisted designs, and may be made from a combination of materials.

As will be apparent from the foregoing description, the present invention offers many advantages over previously known eye drop applicators. In particular, the present invention permits the facile application of drops without having to contact the eye with the fingers, from an applicator which requires no separation of parts to use. Further, the applicator of the invention can be used with one hand.

A further advantage of the invention is the tactile feedback provided by contacting the retractor to the lower lid. This makes it possible for persons with poor vision or poor fine motor control to correctly position the applicator for dispensing drops. The spacing between the eye and the tip that results from the use of the retractor also limits the likelihood of contact with the eye, which could result in injury to the eye or in contamination of the liquid eye drops in the container.

I claim:

1. A bottle for administering liquid eye drops, comprising:
   (a) a container for holding the liquid eye drops;
   (b) a dispensing assembly, said dispensing assembly being coupled to the container and having a passage therethrough for dispensing of the liquid eye drops from the container;

(c) a closure assembly comprising a base portion having means for sealing the passage in the dispensing assembly disposed on an interior surface thereof and means for retracting the lower eye lid of an individual to whom the eye drops are being administered disposed on an exterior surface thereof, wherein said closure assembly is pivotally mounted on the dispensing assembly to permit movement of the closure assembly between a first position in which the passage in the dispensing assembly is sealed by the means for sealing the passage in the dispensing assembly and a second position in which the passage in the dispensing assembly is open to permit dispensing of the liquid eye drops; and (d) means for fixing the closure assembly in the second position.

2. A bottle according to claim 1, wherein the means for fixing the closure assembly in the second position are male and female locking detents.

3. A bottle according to claim 1, further comprising means for fixing the closure assembly in the first and second positions.

4. A bottle according to claim 1, wherein the means for retracting the lower eye lid is a spatulate blade having a curvature which conforms to a human lower lid.

5. A bottle according to claim 1, wherein the means for sealing the passage is a flexible and compressible member affixed on the interior surface of the base portion of the closure assembly.

6. A bottle according to claim 1, wherein the base portion of the closure assembly comprises a substantially circular top portion to which the means for retracting the eye lid is attached, said top portion having opposing side edges and opposing front and back edges; and two opposed skirt portions, said skirt portions extending from the opposing side edges of the circular top portion in a direction opposite to the means for retracting the eye lid while leaving the opposing front and back edges of the top portion free.

7. A bottle for administering liquid eye drops, comprising:

(a) a container for holding the liquid eye drops;

(b) a dispensing assembly, said dispensing assembly being coupled to the container and having a passage therethrough for dispensing of the liquid eye drops from the container; and (c) a closure assembly comprising a base portion having means for sealing the passage in the dispensing assembly disposed on an interior surface thereof and means for retracting the lower eye lid of an individual to whom the eye drops are being administered disposed on an exterior surface thereof, wherein the base portion of the closure assembly comprises a substantially circular top portion to which the means for retracting the eye lid is attached, said top portion having a center, opposing side edges and opposing front and back edges; and two opposed skirt portions, said skirt portions extending from the opposing side edges of the circular top portion in a direction opposite to the means for retracting the eye lid while leaving the opposing front and back edges of the top portion free; and (d) two bearing members, each bearing member being disposed on an interior surface of each of the two opposed skirt portions, wherein the closure assembly is pivotally mounted on the dispensing assembly using the two bearing members to permit movement of the closure assembly between a first position in which the passage in the dispensing assembly is sealed by the means for sealing the passage in the dispensing assembly and a second position in which the passage in the dispensing assembly is open to permit dispensing of the liquid eye drops.

8. A bottle according to claim 7, wherein the top portion of the base portion has a notch formed in front edge of the top portion, and wherein the means for retracting the eye lid is disposed between the center of the top portion and the back edge thereof.

9. A bottle according to claim 8, wherein the dispensing assembly comprises a substantially circular top portion; a skirt portion extending axially downwards from the edge of the top portion of the dispensing assembly; and a dirt seal extending upwards from the top portion of the dispensing assembly, said dirt seal being sized to fit sealingly within the notch in the top portion of the closure assembly.

10. A cap for an eye drop bottle comprising, (a) a dispensing assembly, said dispensing assembly comprising means for coupling the dispensing assembly to a container for holding eye drops and having a passage therethrough for dispensing of the liquid eye drops from container coupled to the dispensing assembly;

(b) a closure assembly comprising a base portion having means for sealing the passage in the dispensing assembly disposed on an interior surface thereof and means for retracting the lower eye lid of an individual to whom the eye drops are being administered disposed on an exterior surface thereof, wherein said closure assembly is pivotally mounted on the dispensing assembly to permit movement of the closure assembly between a first position in which the passage in the dispensing assembly is sealed by the means for sealing the passage in the dispensing assembly and a second position in which the passage in the dispensing assembly is open to permit dispensing of the liquid eye drops; and (c) means for fixing the closure assembly in the second position.

11. A cap according to claim 10, wherein the means for fixing the closure assembly in the second position are male and female locking detents.

12. A cap according to claim 10, further comprising means for fixing the closure assembly in the first and second positions.

13. A cap according to claim 10, wherein the means for retracting the lower eye lid is a spatulate blade having a curvature which conforms to a human lower lid.

14. A cap according to claim 10, wherein the means for sealing the passage is a flexible and compressible member affixed on the interior surface of the base portion of the closure assembly.

15. A cap according to claim 10, wherein the base portion of the closure assembly comprises a substantially circular top portion to which the means for retracting the eye lid is attached; and two opposed skirt portions, said skirt portions extending from opposing side edges of the circular top portion in a direction opposite to the means for retracting the eye lid while leaving opposing front and back edges of the top portion free.

16. A cap for an eye drop bottle comprising:

(a) a dispensing assembly, said dispensing assembly comprising means for coupling the dispensing assembly to a container for holding eye drops and having a passage therethrough for dispensing of the liquid eye drops from the container; and (b) a closure assembly comprising a base portion having means for sealing the passage in the dispensing assembly disposed on an interior surface thereof and means for retracting the lower eye lid of an individual to whom the eye drops are being administered disposed on an exterior surface thereof, wherein the base portion of the closure assembly comprises a substantially circular top portion to which the means for retracting the eye lid is attached, said top portion having a center, opposing side edges and opposing front and back edges; and two opposed skin portions, said skirt portions extending from the opposing side edges of the circular top portion in a direction opposite to the means for retracting the eye lid while leaving the opposing front and back edges of the top portion free; and (c) two bearing members, each bearing member being disposed on an interior surface of each of the two opposed skin portions, wherein the closure assembly is pivotally mounted on the dispensing assembly using the two bearing members to permit movement of the closure assembly between a first position in which the passage in the dispensing assembly is sealed by the means for sealing the passage in the dispensing assembly and a second position in which the passage in the dispensing assembly is open to permit dispensing of the liquid eye drops.

17. A cap according to claim 16, wherein the top portion of the base portion has a notch formed in front edge of the top portion, and wherein the means for retracting the eye lid is disposed between the center of the top portion and the back edge thereof.

18. A cap according to claim 17, wherein the dispensing assembly comprises a substantially circular top portion; a skirt portion extending axially downwards from the edge of the top portion of the dispensing assembly; and a dirt seal extending upwards from the top portion of the dispensing assembly, said dirt seal being sized to fit sealingly within the notch in the top portion of the closure assembly.

* * * * *